United States Patent [19]

Chaudhuri et al.

[11] Patent Number: 5,066,709
[45] Date of Patent: Nov. 19, 1991

[54] BIOADHESIVE COMPOSITION

[75] Inventors: Ratan K. Chaudhuri, Butler; Rama K. Haldar, Randolph; Balgopal Gangadharan, Caldwell, all of N.J.

[73] Assignee: GAF Chemicals Corporation, Wayne, N.J.

[21] Appl. No.: 585,326

[22] Filed: Sep. 20, 1990

[51] Int. Cl.$^5$ .............................................. C08L 39/00
[52] U.S. Cl. .................................. 524/516; 525/327.6
[58] Field of Search ....................... 524/516; 525/327.6

[56] References Cited

U.S. PATENT DOCUMENTS 3,061,569 10/1962 Stoner et al. ........................ 524/516
3,736,274 3/1973 Schoenholz et al. ................ 524/516

Primary Examiner—Joseph L. Schofer
Assistant Examiner—Alex H. Walker
Attorney, Agent, or Firm—Marilyn J. Maue; Joshua J. Ward

[57] ABSTRACT

This invention relates to superior bioadhesive compositions having time extended adhesive properties comprising a non-toxic carrier and a polymer having between about 45 and about 70 weight % of units having the structure

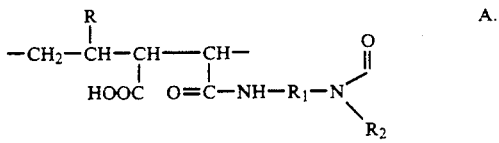

between about 50 and about 30 weight % of units having the structure

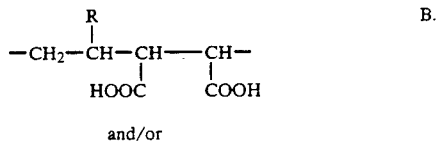

and/or

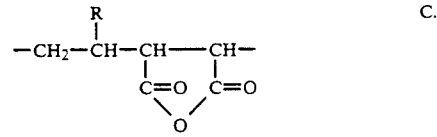

and 2 to 7 weight % of an amine salt containing a lactam functionally derived from A and/or B, wherein R is hydrogen, alkoxy, phenyl, carboxy or —N lactam having from 3 to 6 carbon atoms; $R_1$ is $C_1$ to $C_6$ alkylene and $R_2$ is $C_2$ to $C_4$ alkylene; said copolymer having a number average molecular weight of about 40,000 to about 500,000 and a relatively small particle size. The invention also relates to the method of synthesizing and using the above composition.

13 Claims, No Drawings

BIOADHESIVE COMPOSITION

In one aspect, the invention relates to superior bioadhesives, particularly useful as denture adhesives and adhesives for affixing other devices to mucous membranes. In another aspect the invention relates to a method for preparing the bioadhesive composition.

BACKGROUND OF THE INVENTION

In addition to the routine transient clinical applications of denture adhesives and ostomy devices, there exist psychological needs that require confidence and security during long uninterrupted periods of use or during use under stressful conditions.

While many bioadhesives suitable for attachment of ostomy devices and dentures to mucous membranes are known in the art, the duration of their adhesive properties are relatively short so that frequent replacement of the adhesive is necessary. More specifically, after a few hours of use, a denture adhesive agent interacts with saliva to such a degree that the adhesion force is reduced below 0.3 pounds/inch which is below the limit of failure. Accordingly, much research has been directed to finding a bioadhesive which at least equals the initial holding power of commercially available materials and also has an extended adhesive life of more than 12 hours. Various compounds such as sodium, calcium and magnesium salts of lower alkylvinylether-maleic acid copolymers have been added to bioadhesive formulations to improve strength and durability as disclosed in U.S. Pat. Nos. 3,008,988; 3,736,274; 3,833,518; 3,868,339; 4,183,914; 4,217,342 and 4,217,343. Recently zinc and strontium unmixed salts of lower alkylvinylether-maleic acid copolymers have been developed for this purpose as taught in U.S. Pat. No. 4,758,630. However, these partial salts are effective for considerably less duration than desired, usually functioning not more than a few hours when subjected to stressful use. Accordingly, it is an object of this invention to produce a bioadhesive whose holding power is extended for significantly longer periods of time.

Another object of the invention is to produce an economical and commercially acceptable composition having a long shelf life and high adhesion power.

Another object of the invention is to provide a method of using the improved bioadhesive as a denture fixative.

Still another object is to provide a method of manufacturing a bioadhesive composition.

These and other objects of the invention will become apparent from the following description and disclosure.

THE INVENTION

In accordance with this invention there is provided a bioadhesive composition comprising a non-toxic carrier and a polymer having between about 45 and about 70 weight % units having the formula

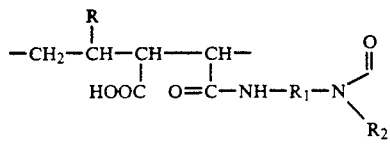

between about 50 and about 30 weight % of units having the structure

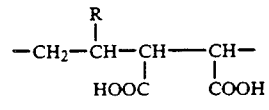

and/or

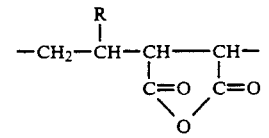

and 2 to 7 weight % of an amine salt having a lactam functionality derived from A and/or B, wherein R is hydrogen, alkoxy, phenyl, carboxyl or —N lactam having from 3 to 6 carbon atoms; $R_1$ is $C_1$ to $C_6$ alkylene and $R_2$ is $C_2$ to $C_4$ alkylene; said copolymer having a number average molecular weight of about 40,000 to about 500,000 and a relatively small particle size.

Preferred of the above compositions are those wherein R is hydrogen or methoxy, $R_1$ is $C_2$ to $C_3$ alkylene, $R_2$ is propylene and the polymer contains from about 20% to about 80% by weight, most preferably from about 30% to about 50% by weight of anhydride units. The particle size of the polymer in the preferred composition is between about 200 and about 450 μm for denture fixative; although smaller or larger particle sizes ranging from 50 to about 1,000 μm are suitable for other uses of the bioadhesive composition.

Representative pharmaceutically acceptable carriers employed in the present compositions can be in the form of a liquid, cream, paste, gel or powder, species of which include powdered cellulose, mineral oil, whey, white petrolatum, polyethylene glycol, polypropylene glycol, paraffin oil, glycerine, petroleum jelly, zinc oxide-eugenol pastes, mixtures of the above components and the like. In addition to the carrier the present polymer can be formulated with adhesive enhancers, if desired examples of which include karaya gum, gum tragacanth, gum arabic, acrylate polymers, carboxymethyl cellulose or an alkali metal salt thereof, and the like. Mixtures including an oil and a gum have been found to be highly efficient.

The above compositions are easily and economically formulated by simply mixing the ingredients under relatively mild conditions at a temperature of between about 30° and about 80° C., preferably between about 50° and about 70° C. with constant stirring for a period of from about 5 minutes to about 1 hour, preferably from about 10 to about 40 minutes or until a homogeneous mixture is obtained. The polymer of the present composition is also easily prepared by introducing into a reactor, a solution of the maleic anhydride copolymer having a number average molecular weight of between about 200,000 and about 2,000,000, and the aminoalkyl lactam in a mole ratio of from about 1:0.45 to 0.75. The solution is reacted at a temperature of from about 40° C. to about b 100° C., preferably from about 50° C. to about 75° C., for a period of 1 to 10 hours usually not more than 5 hours. The resulting product having a molecular weight of between about 40,000 and about 500,000 is then cooled, filtered and dried.

Suitable inert solvents for the reactants include acetone, methyl ethyl ketone, ethyl acetate, and the like and mixtures thereof. During the reaction, the amino alkyl lactam reacts with the maleic anhydride group of the copolymer to open the ring and to produce the corresponding half amide. Also during the reaction, the residual maleic anhydride groups can be hydrolyzed with water to the corresponding diacid at a temperature below about 60° C. When a formulation containing only unit C anhydride groups, to the exclusion of unit B groups, is desired, the formulation is carried out under anhydrous conditions. The resulting anhydride product can be reacted with water until the desired amount of hydrolysis takes place when a mixture of B and C units are required in a specific proportion.

During the reaction of the maleic anhydride copolymer with the aminoalkyl lactam, up to about 7 wt. % of the lactam containing amine salt of unit A and/or unit B, of the following structures, are also formed.

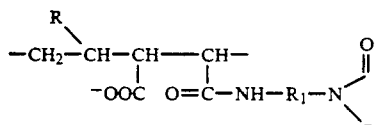

D.

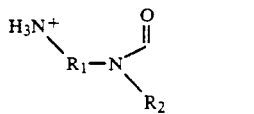

and/or

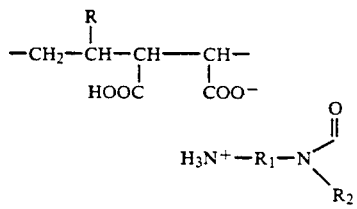

E.

Thus, the polymer of the composition contains at least 2 and may contain up to 5 distinct units arranged in a random distribution. It is important that unit A comprise at least 45% of the polymer since less than this amount produces insufficient hydrogen bonding capability. On the other hand, greater than 70% of unit A reduces the desired carboxyl groups.

Critical elements in formulating the above composition are the use of a alkyl vinyl ether/maleic anhydride copolymer having a number average molecular weight between 40,000 and 500,000; a mole ratio of amino alkyl lactam to copolymer of from 0.45-0.75:1 to insure lactam hydrogen bonding capability and free carboxyl functionality. The overall ratio of polymer to carrier can vary between about 2:1 and about 1:8; although a ratio of between about 1:1 and about 1:4 is preferred.

Representative formulations employing the compositions of this invention are provided in following Example 18. Having thus described the invention, reference is now had to the Examples which illustrate preferred embodiments but which are not to be construed as limiting to the scope of the invention as more broadly described above and in the appended claims.

BIOADHESIVE COMPOSITION

EXAMPLES 1-8

A. The synthesis of eight polymers reported in Table I were carried out under anhydrous conditions by mixing the designated molecular weight GANTREZ® AN powder, i.e. poly(methylvinyl ether/maleic anhydride copolymer and AEP, i.e. N-aminoethyl-2-pyrrolidone dissolved in 50/50 acetone/ethyl acetate solvent.

These solutions were reacted in a glass flask at 55° C., under atmospheric pressure for a period of 4 hours after which the respective polymerized products were recovered by cooling to room temperature, filtering and drying.

The product of example 8 was contacted with water to hydrolyze the anhydride groups of maleic anhydride units to the corresponding dicarboxyl groups.

The above polymeric products were found to contain

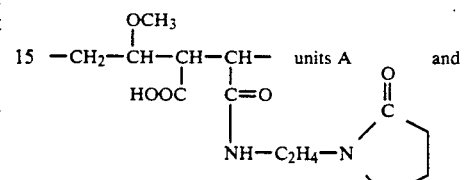

units A and

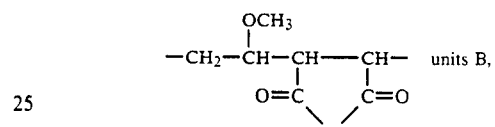

units B, and/or

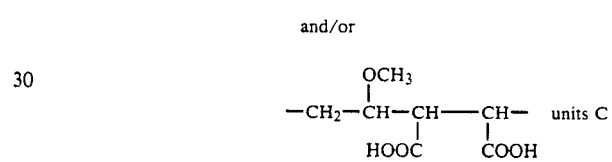

units C as reported in following Table I.

TABLE I

| Example # | Type of GANTREZ ® AN (No. Av. MW) | AEP (moles/mole of GANTREZ ® monomer) | Polymer Product mole % A + mole % B + C (± 3%) |
|---|---|---|---|
| 1 | 119 (216,000) | 0.2 | 20-80 |
| 2 | 119 (216,000) | 0.4 | 40-60 |
| 3 | 119 (216,000) | 0.6 | 60-40 |
| 4 | 119 (216,000) | 0.8 | 80-20 |
| 5 | 139 (990,000) | 0.6 | 60-40 |
| 6 | 149 (1,200,000) | 0.6 | 60-40 |
| 7 | 169 (1,980,000) | 0.6 | 60-40 |
| 8 | 119 (216,000) | 0.6 | 60-40* |

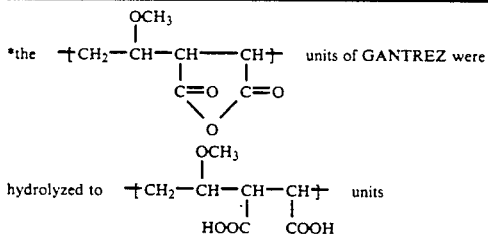

All of the above polymeric products contained from 3.5 to 4.5 wt. % of the ammonium salt D and/or E.

B. Each of the above products was milled to pass through a No. 60 mesh sieve (250 micron particle size) and 3.3 g of the resulting powder dispersed in 6.7 g. petrolatum based carrier at 55°-65° C. with constant stirring so as to provide a polymer to base ratio of 1:2. After 0.5 hour, the resulting cream dispersions were collected as the desired bioadhesive composition.

EXAMPLES 9-17

On an Instron Measuring apparatus, set at a continuous crosshead speed of 2 inches/minute to measure compression and adhesion force for up to b 100 cycles of each 2 g. sample of test adhesive compositions 1-7 B and 3 A. Each sample was spread in about ⅛ inch thickness over the surface of the lower plate of the vertically movable opposing plates of the device. Simulated salivary fluid was applied over the samples so that their surfaces were barely covered. The apparatus was then actuated and the adhesion force, in pounds, were recorded for the 1st, 5th, 10th, 15th, 20th, 40th, 70th and b 100th cycles. The results of these tests are reported in following Table II.

TABLE II

| COMPO-SITION | ADHESIVE FORCE (lbs.) CYCLES* | | | | | | | |
|---|---|---|---|---|---|---|---|---|
|  | 1 | 5 | 10 | 15 | 20 | 40 | 70 | 100 |
| 1B | 1.25 | 1.25 | 0.7 | 0.6 | 0.3 | 0.2 | 0.17 | 0.1 |
| 2B | 1.85 | 1.40 | 0.8 | 0.6 | 0.5 | 0.25 | 0.2 | 0.2 |
| 3B | 2.25 | 1.75 | 0.75 | 0.7 | 0.6 | 0.5 | 0.5 | 0.5 |
| 4B | 1.8 | 1.5 | 0.7 | 0.55 | 0.3 | 0.2 | 0.2 | 0.18 |
| 5B | 1.63 | 1.25 | 0.65 | 0.5 | 0.35 | 0.3 | 0.3 | 0.3 |
| 6B | 1.55 | 1.25 | 0.6 | 0.5 | 0.35 | 0.3 | 0.3 | 0.3 |
| 7B | 1.2 | 0.7 | 0.65 | 0.6 | 0.25 | 0.25 | 0.25 | 0.25 |
| 8B | 3.2 | 2.0 | 1.5 | 1.2 | 1.0 | 1.0 | 1.0 | 0.8 |
| GANTREZ S-97(a) | 1.2 | 1.1 | 0.65 | 0.45 | 0.35 | 0.3 | 0.3 | 0.3 |
| GANTREZ MS-955(b) | 1.15 | 1.2 | 1.1 | 0.9 | 0.8 | 0.6 | 0.45 | 0.4 |

(a) hydrolyzed polymethyl vinyl ether/maleic anhydride
(b) Ca/Na salt of hydrolyzed polymethyl vinyl ether/maleic anhydride
*1 cycle = 1.2 hours of use in vivo An adhesive force of about 0.4 lbs. over extended periods is generally acceptable for a denture adhesive.

EXAMPLE 18

The following are representative of bioadhesive formulations having strong holding power over extended periods of use.

| GENERAL FORMULATIONS | wt. % |
|---|---|
| A. Polymer of Example 8B | 28 |
| Carboxy methyl cellulose | 12 |
| Mineral Oil | 34 |
| White petrolatum | 24 |
| Misc. Additives for color, flavor, etc | 2 |
| B. Polymer of Example 8B | 25 |
| Karaya Gum | 10 |
| Mineral Oil | 32 |
| White petrolatum | 31 |
| Misc. Additives | 2 |
| C. Polymer of Example 3B | 30 |
| Gum Tragacanth | 8 |
| Paraffin Oil | 35 |
| White petrolatum | 25 |
| Misc. Additives | 2 |
| D. Polymer of Example 3B | 32 |
| Gum Arabic | 8 |
| Petroleum jelly | 30 |
| Mineral Oil | 28 |
| Misc. Additive | 2 |
| E. Cream Denture Adhesive |  |
| Mineral Oil | 30 |
| Petrolatum | 25 |
| Sodium carboxymethyl cellulose (adhesive additive) | 20 |
| Colorant | 1 |
| Flavoring Agent | 0.5 |
| Polymer of Example 8B | 23.5 |
| F. Paste Ostomy Adhesive |  |
| Mineral oil (heavy) | 5 |

| GENERAL FORMULATIONS | wt. % |
|---|---|
| Glycerine | 35 |
| Polyvinylpyrrolidone | 20 |
| Carboxymethyl cellulose | 5 |
| Cetyl pyridinium chloride | 0.05 |
| Polymer of Example 8B | 34.95 |
| G. Denture Adhesive Powder |  |
| Gum tragacanth | 40 |
| Gum acacia | 20 |
| Spearmint oil | 0.05 |
| Polymer of Example 8B | 39.05 |
| H. Denture Adhesive |  |
| Polymer of Example 2B | 28 |
| Carboxymethyl cellulose | 12 |
| Mineral oil | 34 |
| White petrolatum | 24 |
| Misc. | 2 |
| I. Denture Adhesive |  |
| Polymer of Example 5B | 32 |
| Gum arabic | 8 |
| Polyethylene glycol (MW 400-8000) | 30 |
| Glycerine | 28 |
| Misc. | 2 |
| J. Denture Adhesive |  |
| Polymer of Example 8B | 33 |
| 60/40 mixture of mineral oil and petrolatum | 67 |
| K. Denture Adhesive |  |
| Polymer of Example 3B | 35 |
| 30-70 mixture of glycerine and PEG* | 65 |

*polyethylene glycol MW 600-8000

The above formulations possess a holding power of at least 1 lb/inch for 12 hours and above 0.5 for 24 hours. It will become obvious from the foregoing disclosure that other formulations using other carriers and other polymers within the scope of this invention can be prepared and formulated in compositions of equally high adhesive strength and durability. For example, copolymers of maleic anhydride and styrene, maleic anhydride and vinyl pyrrolidone, maleic anhydride and ethylene or maleic anhydride and acrylic or methacrylic acid can be substituted for the above copolymer and other alkyl amino lactams, such as aminobutyl caprolactam, aminopropyl pyrrolidone, can be substituted in the polymer synteses reaction and their products used in any of the above formulations A-G to provide useful bioadhesive compositions without departing from the scope of this invention.

What is claimed is:

1. A bioadhesive composition comprising a non-toxic carrier and a polymer comprising between about 45 and about 70 weight % of units having the structure

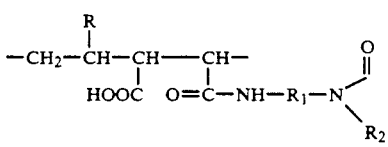

between about 50 and about 30 weight % of units having the structure

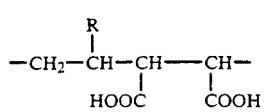

-continued
and/or

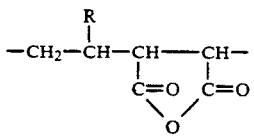
C.

and 2 to 7 weight % of an amine salt containing a lactam functionality derived from A and/or B, wherein R is hydrogen, alkoxy, phenyl, carboxyl or —N lactam having from to 6 carbon atoms; $R_1$ is $C_1$ to $C_6$ alkylene and $R_2$ is $C_2$ to $C_4$ alkylene; said copolymer having a number average molecular weight of about 40,000 to about 500,000 and a relatively small particle size.

2. The composition of claim 1 wherein said carrier is a mixture of an oil and a natural gum.

3. The composition of claim 2 wherein said carrier mixture contains an oil selected from the group of mineral oil, white petrolatum vegetable oil, glycerin, and paraffin oil.

4. The composition of claim 1, 2 or 3 wherein said carrier additionally contains carboxymethyl cellulose or polyvinylpyrrolidone.

5. The composition of claim 1, 2 or 3 wherein R of the polymer is methoxy or hydrogen.

6. The composition of claim 1, 2 or 3 wherein R is methoxy, $R_1$ is lower alkylene and $R_2$ is —$C_3H_6$—.

7. The composition of claim 1, 2 or 3 wherein the mole ratio of carrier to polymer is between about 2:1 and about b 1:8.

8. The composition of claim 7 wherein said mole ratio is between about 1:1 and about 1:4.

9. The composition of claim 1 wherein said composition is a paste.

10. The composition of claim 1 wherein said composition is a powder.

11. A polymeric product having random distribution comprised of (a) 50-70 weight % of units

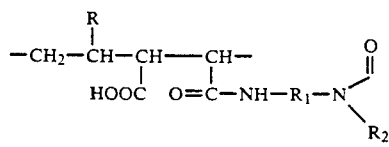
A.

(b) 50-30 weight % of units

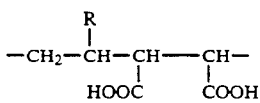
B.

and/or

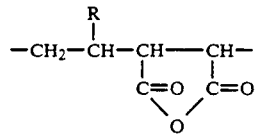
C.

and (c) 2 to 7 weight % of ammonium salt of said unit A and/or B defined by the formulae

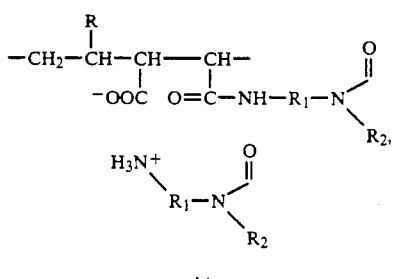
D.

and/or

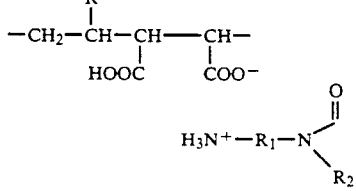
E.

12. The polymeric product of claim 11 wherein the product comprises a major portion of unit A, at least 20 weight % of unit C and between about 3 and about 5 weight % of said ammonium salt unit.

13. The polymeric product of claim 11 wherein the product comprises a major portion of unit A, at least 30 weight % of unit C, between about 0 and about 20 weight % of unit B and between about 3 and about 5 weight % of said ammonium salt unit.

* * * * *